(12) United States Patent
Brown et al.

(10) Patent No.: US 7,887,328 B2
(45) Date of Patent: *Feb. 15, 2011

(54) METHOD FOR WHITENING TEETH

(75) Inventors: Damon J. Brown, Boston, MA (US); Graham K. Philp, Jr., Naples, FL (US); Adam Diasti, Tampa, FL (US)

(73) Assignee: Dentovations Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/293,499

(22) Filed: Dec. 5, 2005

(65) Prior Publication Data

US 2006/0141423 A1    Jun. 29, 2006

Related U.S. Application Data

(63) Continuation of application No. PCT/US03/17631, filed on Jun. 5, 2003.

(51) Int. Cl.
*A61C 5/00* (2006.01)
*A61K 7/16* (2006.01)

(52) U.S. Cl. .......................... 433/216; 424/49
(58) Field of Classification Search ................. 433/215, 433/216; 424/49, 53
See application file for complete search history.

(56) References Cited

U.S. PATENT DOCUMENTS

| | | | |
|---|---|---|---|
| 3,278,520 A | 10/1966 | Klug | |
| 3,278,521 A | 10/1966 | Klug | |
| 3,567,823 A | 3/1971 | Yamaga et al. | |
| 3,771,881 A * | 11/1973 | Swenson | ....................... 401/75 |
| 4,556,561 A | 12/1985 | Brown et al. | |
| 4,611,611 A * | 9/1986 | Beal, Jr. | ...................... 132/320 |
| 4,661,070 A | 4/1987 | Frieman | |
| 4,684,517 A | 8/1987 | Clipper et al. | |
| 4,976,955 A | 12/1990 | Libin | |
| 4,980,152 A | 12/1990 | Frazier et al. | |
| 4,983,380 A | 1/1991 | Yarborough | |
| 5,000,942 A | 3/1991 | Libin | |
| 5,009,885 A | 4/1991 | Yarborough | |
| 5,032,178 A | 7/1991 | Cornell | |
| 5,084,268 A | 1/1992 | Thaler | |

(Continued)

FOREIGN PATENT DOCUMENTS

| | | |
|---|---|---|
| EP | 0539315 | 4/1993 |
| WO | WO 9940870 A1 | 2/1999 |
| WO | WO 0126576 A1 | 10/2000 |

OTHER PUBLICATIONS

International Search Report dated Oct. 7, 2003 in parent application No. PCT/US03/17631, filed Jun. 5, 2003 (6 pgs.).

*Primary Examiner*—Ralph A. Lewis
(74) *Attorney, Agent, or Firm*—Shlesinger, Arkwright & Garvey LLP

(57) ABSTRACT

Tooth whitening compound includes a whitener and a carrier selected for adhering the carrier and whitening composition to a user's teeth. The whitening compound may be applied by the method including painting, washing, sponging, coating, daubing, spraying, wiping, rubbing, and by any movement relative to a horizontal or vertical axis of the user's tooth. The whitening compound may be sufficiently viscous to adhere to a user's teeth, in use, without a mechanical retaining device. The whitening compound may be a semi-solid or a solid compound at ambient temperatures.

10 Claims, 2 Drawing Sheets

U.S. PATENT DOCUMENTS

| | | |
|---|---|---|
| 5,139,768 A | 8/1992 | Friedman |
| 5,171,564 A | 12/1992 | Nathoo et al. |
| 5,208,010 A | 5/1993 | Thaler |
| 5,217,710 A | 6/1993 | William et al. |
| 5,234,342 A | 8/1993 | Fischer |
| 5,264,205 A | 11/1993 | Kelly |
| 5,279,816 A | 1/1994 | Church et al. |
| 5,290,566 A | 3/1994 | Schow et al. |
| 5,302,375 A | 4/1994 | Viscio |
| 5,310,563 A | 5/1994 | Curtis et al. |
| 5,372,802 A | 12/1994 | Barrows et al. |
| 5,376,006 A | 12/1994 | Fischer |
| 5,395,241 A | 3/1995 | Kandelman |
| 5,403,577 A | 4/1995 | Friedman |
| 5,403,578 A | 4/1995 | Gordon |
| 5,409,631 A | 4/1995 | Fischer |
| 5,425,953 A | 6/1995 | Sintov et al. |
| 5,437,858 A | 8/1995 | Hungerbach et al. |
| 5,611,687 A * | 3/1997 | Wagner ................. 433/80 |
| 5,614,174 A | 3/1997 | Hsu et al. |
| 5,631,000 A | 5/1997 | Pellico et al. |
| 5,690,912 A | 11/1997 | Campbell et al. |
| 5,693,315 A | 12/1997 | Bevilacqua |
| 5,698,182 A | 12/1997 | Prencipe et al. |
| 5,708,052 A | 1/1998 | Fischer et al. |
| 5,718,886 A | 2/1998 | Pellico |
| 5,746,598 A | 5/1998 | Fischer |
| 5,766,574 A | 6/1998 | Christina-Beck et al. |
| 5,780,015 A | 7/1998 | Fisher et al. |
| 5,785,527 A | 7/1998 | Jensen et al. |
| 5,785,957 A | 7/1998 | Losee et al. |
| 5,792,446 A | 8/1998 | Ashley |
| 5,797,749 A | 8/1998 | Bertolotti et al. |
| 5,814,304 A | 9/1998 | Wong et al. |
| 5,820,852 A | 10/1998 | Burgess et al. |
| 5,824,289 A | 10/1998 | Stoltz |
| 5,846,570 A | 12/1998 | Barrow et al. |
| 5,849,266 A | 12/1998 | Friedman |
| 5,849,269 A | 12/1998 | Burgess et al. |
| 5,851,512 A | 12/1998 | Fischer |
| 5,855,870 A | 1/1999 | Fischer |
| 5,858,332 A | 1/1999 | Jensen et al. |
| 5,879,691 A | 3/1999 | Sagel et al. |
| 5,891,453 A | 4/1999 | Sagel et al. |
| 5,902,568 A | 5/1999 | Ryles et al. |
| 5,922,307 A | 7/1999 | Montgomery |
| 5,928,628 A | 7/1999 | Pellico |
| 5,985,249 A | 11/1999 | Fischer |
| 6,030,222 A | 2/2000 | Tarver |
| 6,036,493 A | 3/2000 | Sharma |
| 6,083,421 A * | 7/2000 | Huang et al. ........... 252/186.28 |
| 6,102,696 A | 8/2000 | Osterwalder |
| 6,149,211 A * | 11/2000 | Losee et al. ................. 292/258 |
| 6,183,251 B1 | 2/2001 | Fischer |
| 6,290,417 B1 * | 9/2001 | Kaminski ................... 401/123 |
| 6,312,666 B1 | 11/2001 | Oxman et al. |
| 6,419,906 B1 * | 7/2002 | Xu et al. ........................ 424/53 |
| 6,439,885 B2 * | 8/2002 | Antler ........................ 433/142 |
| 6,450,179 B2 * | 9/2002 | Bengis ....................... 132/297 |
| 6,517,350 B2 | 2/2003 | Diasti et al. |
| 2002/0004190 A1* | 1/2002 | Diasti et al. ................. 433/215 |
| 2002/0047222 A1 | 4/2002 | Philp |
| 2002/0064753 A1 | 5/2002 | Philp |
| 2003/0003059 A1* | 1/2003 | Dana .......................... 424/49 |
| 2005/0008584 A1* | 1/2005 | Montgomery ................ 424/53 |
| 2005/0255054 A1 | 11/2005 | Philp et al. |
| 2005/0260142 A1 | 11/2005 | Philp et al. |
| 2006/0141422 A1 | 6/2006 | Philp et al. |
| 2006/0141423 A1 | 6/2006 | Brown et al. |
| 2007/0009857 A1 | 1/2007 | Philp et al. |
| 2009/0148815 A1 | 6/2009 | Philp et al. |
| 2009/0325129 A1 | 12/2009 | Brown et al. |

* cited by examiner

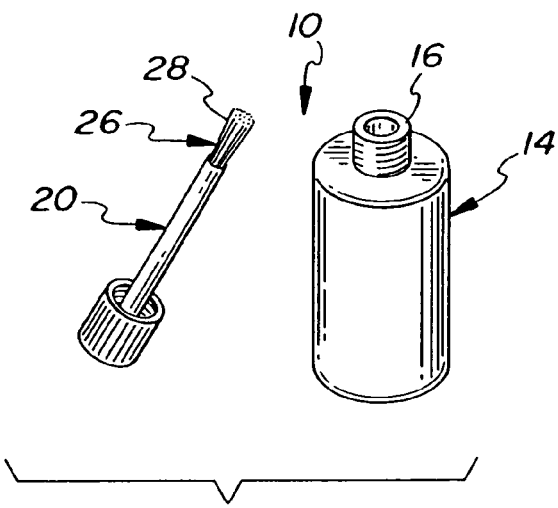
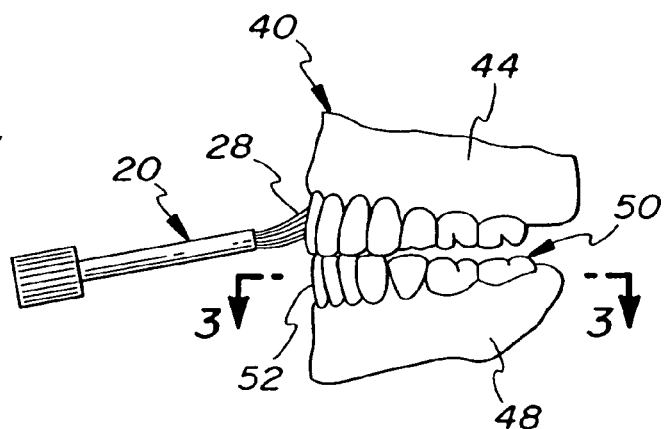
FIG. 1
FIG. 2
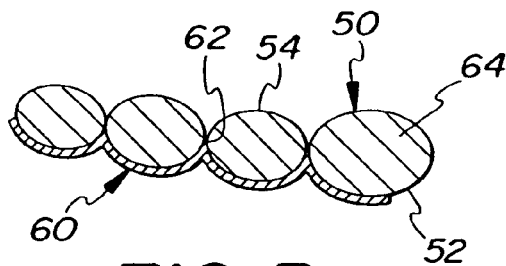
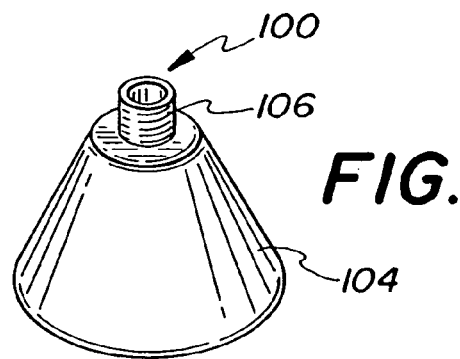
FIG. 3
FIG. 4
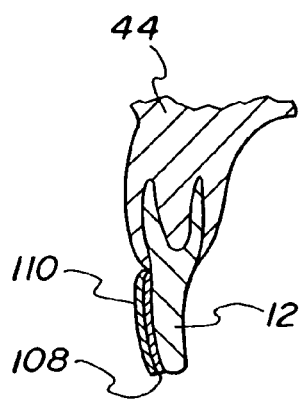
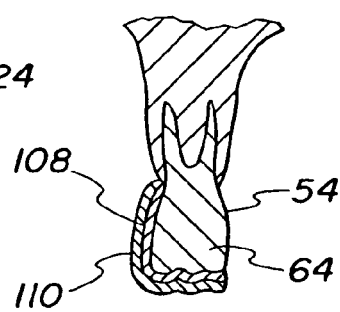
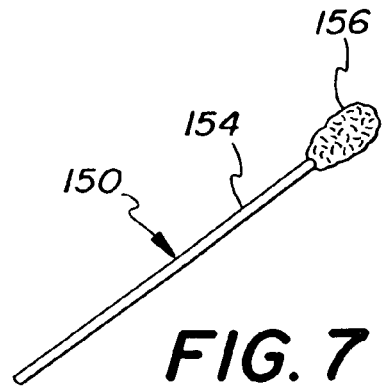
FIG. 5
FIG. 6
FIG. 7

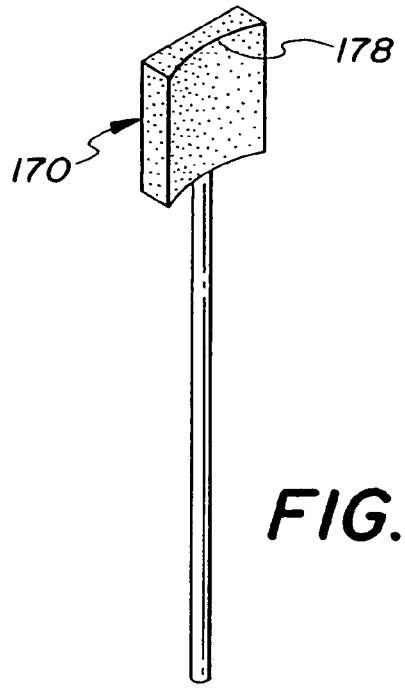
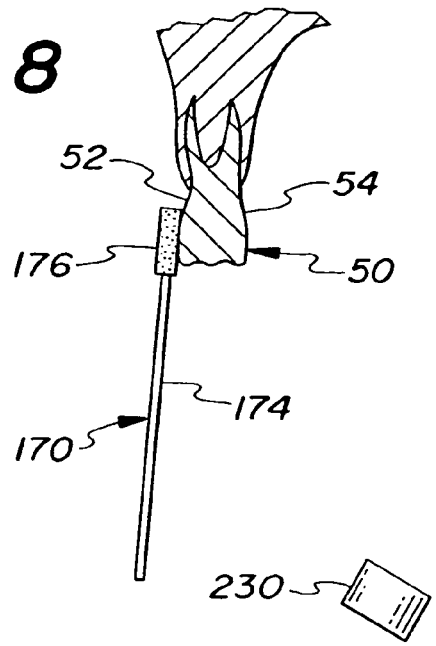
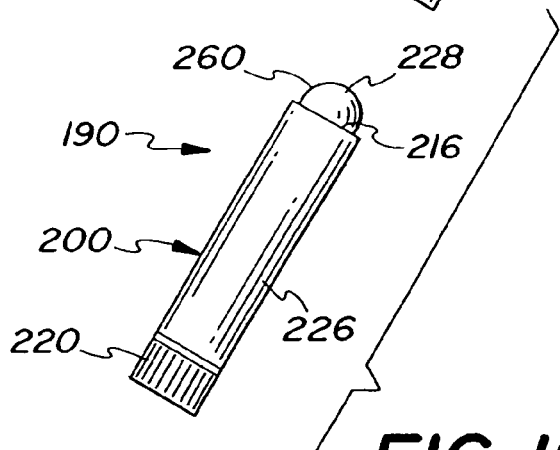
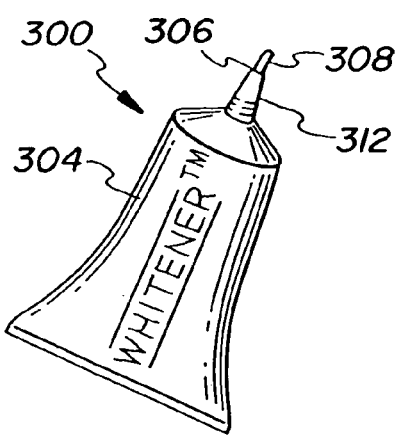
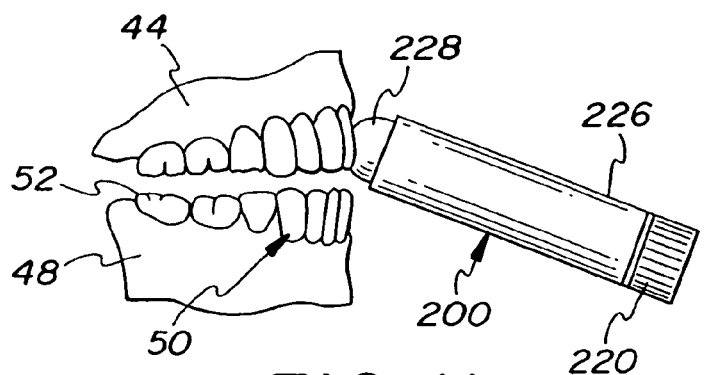

METHOD FOR WHITENING TEETH

CROSS-REFERENCE TO RELATED APPLICATION

This application is a continuation of Application No. PCT/US2003/017631, filed Jun. 5, 2003, which is incorporated herein by reference.

This application relates to applicant's concurrently filed application Ser. No. 11/293,497, entitled "METHOD AND APPARATUS FOR TOOTH WHITENING", filed Dec. 5, 2005, and which is incorporated herein by reference.

FIELD OF THE INVENTION

The invention relates to systems and methods for treating teeth. More specifically, the invention relates to a system (e.g., a novel delivery system) for delivering a tooth whitener to a tooth and a method for whitening teeth. The invention likewise relates to a system and method for whitening teeth without the use of a mouth tray or other retaining device of the type which retains the tooth whitener in place against the teeth during use.

BACKGROUND OF THE INVENTION

Tooth whiteners are known. Conventional tooth whiteners are laborious, unwieldy, and expensive.

Conventional tooth whitening methods are complicated and expensive, and, hence, are limited to a small portion of the population.

In one typical method, the user whose teeth are to be whitened must first visit a dentist in order to have a mouth tray made which is molded to fit that user's teeth from a cast made from an impression.

After the conventional steps of producing the mouth tray have been completed, then the mouth tray is given to the user, along with the tooth whitening compound(s).

In some tooth whitening methods, the user then takes the tooth whitening compounds home, and uses them in conjunction with the mouth tray in the privacy of his or her home.

In use, the mouth tray is at least partially filled by the user with the tooth whitening compound provided by the dental practitioner.

The user must then take the proper mouth tray for the respective upper or lower jaw and press the mouth tray filled with whitening compound up (or down) against the teeth to be whitened.

The user then holds the mouth tray filled with the compound in place against the teeth for a specified period of time.

After the specified period of time, the user removes the mouth tray and the bulk of the compound, and discards the used whitening compound.

Typically, the whitening procedure is a multi-day procedure.

U.S. Pat. No. 5,879,691 to Sagel et al. discloses a delivery system for a tooth whitener using a strip of material having low flexural stiffness.

Some known conventional whitening methods (e.g., the type of methods that utilize either a traditional tray or an adhesive strip) require that the whitening compound be forced on the gingival tissue in the region adjacent to the teeth to be whitened. That forcing whitening compound on the gingival tissue may result in a burning sensation to that tissue.

Many known whitening compounds have the drawback that they dry out the teeth, in use, owing to the whitening compounds drawing moisture out of the teeth. Such dried out teeth are more sensitive to hot and cold. Accordingly, many prior art whiteners required desensitizers (desensitizing compounds) so that the patients would not be bothered by their temperature-sensitive dried out teeth.

OBJECTS AND SUMMARY OF THE INVENTION

It is an object of the invention to overcome the drawbacks of the prior art methods, compounds, and devices.

A further object of the invention is to provide a tooth whitening method that is easier to use, more cost effective, and available to a greater percentage of the population.

A still further object of the invention is to provide a tooth whitening method that eliminates the need for mouth trays which fit the respective upper and lower sets of teeth in the user's mouth for retaining the whitening compound against the teeth to be whitened, as in the conventional methods.

Yet another object of the invention is to allow the whitening compound to adhere to the user's teeth, thus eliminating entirely the need for a mouth tray to retain the tooth whitening compound.

Yet another object of the invention is to provide a tooth whitening method which is easier to use than the known methods.

Another object of the invention is to provide a tooth whitening system and method which dries out the user's teeth less than conventional whitening methods, so that the use of tooth desensitizing agents in the whitening compound may be reduced or eliminated.

A further object of the invention is to provide a tooth whitener system and method that directly applies a whitening agent onto the surfaces of the user's teeth, thus eliminating the need for any type of tray or other mechanical retention device to retain the whitening agent on the surfaces of the teeth.

Another object of the invention is to provide a whitener delivery system which reduces or eliminates the discomfort or burning sensation of the user's gingival tissue that may occur when using prior art delivery systems.

Yet another object of the invention is to provide a tooth whitening system in which the whitening compounds are applied substantially directly to the facial and labial surfaces of the teeth to be whitened.

Another object of the invention is to provide a tooth whitening system and method which reduce or eliminate the annoyance and inconvenience of using and wearing pre-made trays or adhesive-strip type products.

A still further object of the invention is to provide a tooth whitening system and method which are more effective than known over-the-counter whitening methods requiring the use of boil-and-bite type trays that do not fit the teeth properly and, hence, are often ineffective and result in less than desirable tooth whitening.

In summary, the invention provides a tooth whitening method which can be performed without the use of a mouth tray for retaining a tooth whitening compound against the user's teeth.

It is another object of this invention to have a delivery system where the whitening compound is directly applied onto the tooth in a solid or semi-solid state. The whitening compound may be applied in a manner similar to the use of a tube of lipstick.

It is further object of the invention to have the whitening compound in a dispenser, which can be utilized without the use of a mirror and without the need for the user to hold the lips away from the teeth any longer than it takes to apply the whitening compound onto the tooth.

It is a further object of the invention to eliminate the need for whitening mouth trays, applicator brushes, and bottles which hold the whitening compound.

In summary the invention pertains to delivering a whitening compound against the tooth surface in a solid/semi-solid state in a device resembling a tube of lipstick or a mechanical pencil design.

It should be understood that relative terms such as up, and down are for convenience only and are not intended to be limiting.

It should likewise be understood that throughout the specification the features and advantages described in connection with the tooth whitening system apply equally to the features and advantages of the method of whitening teeth described herein.

BRIEF DESCRIPTION OF THE DRAWINGS

FIG. 1 is an elevational view of a tooth whitening system according to the invention;

FIG. 2 shows the applicator of FIG. 1 in use;

FIG. 3 shows a first layer or whitening agent as applied to the user's teeth, which is a cross sectional view of teeth taken along line 3-3 of FIG. 2;

FIG. 4 illustrates a further container for use with a further embodiment of a tooth whitening system according to the invention;

FIG. 5 is a cross sectional view of a user's incisor with a whitening layer on the front surface of the tooth;

FIG. 6 illustrates a user's molar with a whitening layer on the front and lower face of the tooth;

FIG. 7 shows a further embodiment of an applicator for use with the systems according to the invention;

FIG. 8 shows a still further embodiment of an applicator for use with the systems according to the invention;

FIG. 9 is a front perspective view of the applicator of FIG. 8;

FIG. 10 shows another applicator according to the invention;

FIG. 11 shows the FIG. 10 applicator, in use; and

FIG. 12 shows another applicator according to the invention.

The term painting is intended to cover all manner of applying a layer of the whitening compound to a tooth, the term painting including, but not limited to brushing, sponging, coating, daubing, spraying, wiping, rubbing, and applying by movement relative to the tooth (i.e., any movement relative to a vertical or horizontal axis of a tooth) yielding a layer of whitening compound on the tooth. The movement relative to the tooth is not intended to be limited to movement toward and away from the gum. For example, spraying and daubing may be carried out with little or essentially no movement along an axis that is at an acute angle relative to the longitudinal axis of the tooth (e.g., a central, substantially vertical axis of a user's tooth).

DETAILED DESCRIPTION OF THE INVENTION

FIGS. 1-9

FIGS. 1-3 illustrate an embodiment of a tooth whitening delivery system 10 according to a first preferred embodiment of the invention.

Tooth whitening system 10 includes a container 14 for holding a whitening agent or first whitening compound 60. Container 14 may be provided with a resealable opening 16 for repeated access to the inside and, hence, the contents of container 20.

A brush 20 having a handle 24 and bristles 26 may be provided for applying the whitening agent held in container 20.

Bristles 26 may be configured for being held by a user when applying the whitening agent to the user's teeth by use of bristles 28.

Container 20 may be disposable, or may take another form, as described below.

FIG. 3 illustrates the user's or user's jaw 40 including an upper jaw 44 and a lower jaw 48.

Teeth 50 include an outer surface 52 and a corresponding inner surface 54.

In some cases, only outer surface 52 will be whitened by use of the whitening agent 60, as it is outer surface 52 which is visible when the user's lips are drawn back exposing teeth 50.

FIG. 2 illustrates how brush 20 is applying the whitening agent on outer surface 52 of teeth 50. It should be noted that bristles 28 may be configured and sized so as to reach all exposed surfaces of teeth 50. Preferably, the viscosity of compound 60 is selected so that the whitening agent 60 may be applied directly to all the exposed tooth surfaces which the user desires to whiten. In use, the user may dispense, such as by painting on, a desired quantity of whitening compound 60, holding brush 20 as shown in FIG. 1, and apply sufficient pressure to force whitening compound 60 into crevices 62, for example, as desired. One or more teeth 50 may have whitening compound 60 applied to them.

A single coat or multiple coats or layers of whitening agent 60 may be applied.

Whitening agent 60 is formulated so that it need not be covered, in use, by a device, such as a tray or tape, as the formulation is selected so that the whitening agent 60 adheres to the user's teeth.

FIGS. 2 and 3 illustrate the manner in which the whitening agent 60 or the bristles 26 or both are selected so that whitening agent or first layer 60 extends into the exposed crevices 62 between teeth 64, for example. FIG. 3 shows whitening agent 62 applied to the outer surfaces 52 of tooth 64.

Whitening agent 60 of FIGS. 1-3 has been successfully used with only one layer of compound 60 as the whitening agent. Of course, the user may apply a thin layer 108 of compound 60, and then apply more whitening compound 60 to thicken the initial layer, yet both "layers" would be, in effect, a single thicker layer of the same compound 60. In use, there was no apparent burning or ill effects of whitening agents 60 when whitening agent 60 contacted the mouth tissue.

FIGS. 4-6 illustrate another preferred embodiment of a whitening system 100 according to the invention. Whitening system 100 includes a container 104 having an opening 106 for providing access to the contents of container 104.

FIG. 5 illustrates how one of a user's incisors 124 is whitened. In the case of incisor 124 the whitening agent 108 may be applied only to the outer surface 52 of incisor Typically, a user will find it unnecessary to whiten the inner surfaces 54 of his or her incisors 124, as the inner surfaces of the user's incisors 124 are rarely visible to others, for example.

FIG. 6 illustrates the case where a user would like to whiten the outer surface 52 as well as the lower surfaces of his or her teeth, such as an illustrated molar 64. In that case, whitening agent 108 is applied to outer surface 52 as well as to the lower surface of the illustrated upper molar 64.

In the case where the user would like to whiten the inner surface 54 of molar 64, the whitening agent 108, will be applied to inner surface 54 of the molar.

FIG. 7 illustrates another preferred embodiment of an applicator 150, according to the invention.

Applicator 150 includes a handle 154 and a material 156 disposed at one of its ends. The material 156 may be a soft absorbent material such as cotton, and applicator 150 may take the form of a cotton swab.

Applicator 150 may be disposable. Applicator 150 may be a cotton swab such as a Q-TIP® brand cotton swab.

FIGS. 8 and 9 illustrate yet another preferred embodiment of an applicator 170 according to the invention.

Applicator 170 includes a handle 174 and a material 176 disposed at one of its ends.

Material 176 may be shaped to conform to the shape of the surface of tooth 50 to enhance the application of whitening agent on tooth 50.

Material 176 may be made of a foam material, such as cellular foam.

Applicator 170 may be disposable, in a manner similar to the other applicator embodiments.

The embodiments of FIGS. 7-9 may be used with either of the dispensers of FIGS. 1-3 or FIGS. 4-6. In such a case, the user may dispense a desired quantity of solid whitening agent or semi-solid whitening agent 60 or 108 or 110 (or one or more of agents 60 and 108 and 110) onto applicator 150 or 170, respectively, for example.

The viscosity of one or more of whitening agents 60,108 may be varied depending on the intended use, as described in detail below.

It is contemplated that in any of the embodiments of FIGS. 1-9 any suitable viscous, solid or semi-solid whitening agent may be used that can whiten without irritating the mouth tissues.

In a preferred embodiment of the invention, whitening agent 60 may have the following range of compositions.

Whitening Agent Composition A2

To Yield 100 ml of Composition

| Ethanol (ethyl alcohol) | balance ml |
| Urea Peroxide | .001-40 g |
| Resin | .001-30 g |
| Hydroxyl propyl cellulose | .001-20 g |
| total | 100 ml |

A further preferred embodiment of the whitening agent follows.

Whitening Agent Composition A4

Total Yield 100 ml of Composition

| Ethanol (ethyl alcohol) | balance ml |
| Urea Peroxide | 8 g |
| Resin | 10 g |
| Hydroxyl propyl cellulose | .5 g |
| total | 100 ml |

Whitening agent 110 of composition A3 may be made with 100% pure undenatured ethyl alcohol and 98% pure urea peroxide.

Rosin may be substituted for resin in all formulas.

Urea hydrogen peroxide may be substituted for urea peroxide in all formulas.

Whitening agents may be formulated as follows:

Whitening Agent Composition A5

Total Yield 100 ml of Composition

| Rosin | .001-30 g |
| Urea hydrogen peroxide | .001-40 g |
| Hydroxypropyl cellulose 1500 cps | .001-20 g |
| Ethyl alcohol (95%) | balance ml |
| Total Volume | 100 ml |

The following is an example of a tooth whitening compound that has been formulated in accordance with the invention.

The following is the formulation of a procedure for making 100 ml of a Solution No. 16.

In the following formula, the resin, the urea hydrogen peroxide USP, and the hydroxypropyl cellulose 1500 cps are all expressed as a weight per volume (w/v; i.e., g/100 ml) and the ethanol 95 was added in a quantity as needed (q.s.) to yield the desired 100 ml of whitening agent.

Whitening Agent Composition of Solution No. 16

Total Yield 100 ml of Composition

| Rosin | 12.5 g |
| Urea hydrogen peroxide | 8.0 g |
| Hydroxypropyl cellulose 1500 cps | 0.5 g |
| Ethyl alcohol (95%) | balance ml |
| Total Volume | 100 ml |

Solution No. 16 was formulated as follows to yield 100 ml of product:
1. Dissolve 12.5 g of resin in 75 ml of the ethanol in a beaker having a spin bar therein;
2. The spin bar was spun using the spinning device (stirrer) of an unheated hot plate of the type having a magnetic stirrer disposed therein, the spinning was continued until the unheated rosin and ethanol solution was clear;
3. 8 g of the urea hydrogen peroxide were weighed out and ground into a fine powder using a mortar and pestle, added to the rosin and ethanol solution, and then stirred on the spinning device. A cloudy solution resulted.
4. As the rosin and ethanol solution was spinning, the 0.5 g of hydroxypropyl cellulose was added gradually (sprinkled into the vortex of the spinning solution resulting from the magnetic stir bar) in small amounts at a time. The spinning was continued for about an hour until the solution began to gel. Enough ethyl alcohol (95%) was added q.s. to bring the volume up to 100 ml, and the spinning was continued.
5. The mixed solution was put in a refrigerator (at about 40° F.) and left overnight (i.e., about 19-20 hours) to allow the solution to completely hydrolyze.
6. The refrigerated solution was removed from the refrigerator and again spun at room temperature at about 70° F.) for about 30 minutes to thoroughly mix the solution.

The prepared solution was then put into the desired containers.

It should be noted that in Step 4 of spinning the solution having the rosin, the urea hydrogen peroxide 1500 cps, and the hydroxypropyl cellulose, the added materials may not thoroughly dissolve. It appears that the step of allowing the solution to sit overnight in the refrigerator for a period of time, and then remixing the solution succeeds in yielding a homogeneous solution with the added materials dissolved and dispersed throughout.

The following is the formulation of a Solution No. 18 that has been made.

Whitening Agent Composition of Solution No. 18

Total Yield 60 ml (i.e., 51.43 g) of Composition

| Rosin | 7.5 g |
|---|---|
| Urea hydrogen peroxide | 3.6 g |
| Hydroxypropyl cellulose 1500 cps | 0.3 g |
| Ethyl alcohol (95%) | 40.0 g |
| Spearmint Extract (1 drop) | 0.03 g |
| Total Weight | 51.43 g |

Thus, Solution No. 18 can be expressed on a weight per weight (w/w) basis of about 14.6% rosin; 7.0% urea hydrogen peroxide; 0.6% hydroxypropyl cellulose 1500 cps; 77.8% ethyl alcohol; and 0.06% spearmint extract; the total is not exactly 100% owing to the rounding of the percentages to one (1) significant digit.

Solution No. 18 was prepared in a manner analogous to that as described above in connection with the preparation of Solution No. 16.

It will be seen that the achievement of a tooth whitening delivery system has been realized that provides for directly applying a whitening agent onto the surfaces of the teeth, thus eliminating the need for any type of tray or other type of carrier.

In other words, the invention achieves the object of an elegantly simple solution to the problem of expensive laborious and unwieldy tooth whitening systems that made such unavailable to the vast majority of the user population.

The tooth whitening system achieves the goal of applying and retaining a whitening agent against the user's teeth without the need for a mouth tray or other retaining wall or retaining means that had previously been necessary.

The method may be carried out without the use of a mouth tray, mold, or other retaining wall for keeping the whitening agent in place against the teeth. Such trays have previously been required to protect the soft mouth tissue as well.

The whitening compound in one basic form includes a combined carrier that adheres to the user's teeth, and a whitening agent.

The inventive method eliminates the traditional use of any form of mouth trays for teeth whitening.

The invention further includes a teeth whitener having a novel carrier that temporarily adheres to the tooth for the purpose of whitening the tooth with or without a desensitizing agent.

The tooth whitener is bound in the resin and is released or is activated by moisture or water from the mouth (i.e., from the saliva in the mouth) rather than by the tooth structure itself. It is believed that owing to the whitening compound being released throughout the thickness of the applied resin, the active layer is against the tooth being whitened, which tooth is buried in the resin. The hydrogen peroxide or peroxide compound against the mouth tissue is neutralized or broken down by the water in the saliva. In that manner, the tissue is unharmed.

It has been observed that the whitening compound is released (activated throughout the resin for a period of about or about 10-30 minutes). This is seen as an effervescing over the coated tooth surfaces. This can be easily removed by brushing; and additional application(s) of the whitening compounds may be applied. It may be that the whitening compound is activated (released) against the tooth surfaces for a much longer time than the time period during which the effervescence is observed.

The following formulations are in accordance with the invention.

A whitening compound suitable for applying to teeth may comprise by weight percent:

Whitening Agent Composition D1

A further whitening compound may comprise in weight percent:
  a) Ethyl Alcohol 95% is about 15-85% (e.g., 76.36%);
  b) Synthetic Resin (FORAL NC) is about 0.001-65% (e.g., 13.76%);
  c) Urea Hydrogen Peroxide or PVP Hydrogen Peroxide is about 0.001-45% (e.g., 8.81%);
  d) Hydroxypropylcellulose (KLUCEL HF PHARMA) is about 0.001-20% (e.g., 0.55%);
  e) Peppermint Oil is about 0.001-5% (e.g., 0.15%);
  f) Menthol is about 0.001-5% (e.g., 0.22%); and
  g) Aspartame® is about 0.001-5% (e.g., 0.15%).

Peppermint Oil, Menthol, and Aspartame® all only used for flavoring and do not affect the efficacy of the product. Resin compound can be easily brushed off or it will wear off after several hours.

Ethyl Alcohol suppliers may include Chemisphere Corp., St. Louis, Mo., U.S.A;

Synthetic Resin (FORAL NC) suppliers may include Hercules Chemical, PINOVA Division Brunswick, Ga., U.S.A.;

Urea Hydrogen Peroxide or PVP Hydrogen Peroxide suppliers may include Urea Hydrogen Peroxide from American International Chemical, Natick, Mass., U.S.A.; or PVP Hydrogen Peroxide from International Specialty Products, Wayne, N.J., U.S.A.;

Hydroxypropylcellulose (KLUCEL HF PHARMA) suppliers may include Hercules Incorporated, Aqualon Division, Wilmington Del., U.S.A.;

Peppermint Oil suppliers may include PCCA, Houston, Tex., U.S.A.;

Menthol suppliers may include PCCA, Houston, Tex., U.S.A.; and

Aspartame® suppliers may include PCCA, Houston, Tex., U.S.A.

Whitening Agent Composition D1 vs. Conventional Brush-On Whitening Product

|  | TOOTH WHITENING AGENT COMPOSITION D1 | CONVENTIONAL BRUSH-ON WHITENING PRODUCT |
|---|---|---|
| Solution | 9% (by weight) Carbamide Peroxide (Urea hydrogen peroxide or PVP Hydrogen peroxide) No Carbopol No Glycerin | 3-4% Carbamide Peroxide |
| Ease of Application | Directly apply to teeth | Must first dry teeth, Directly apply to teeth |

-continued

|  | TOOTH WHITENING AGENT COMPOSITION D1 | CONVENTIONAL BRUSH-ON WHITENING PRODUCT |
|---|---|---|
| Mode of Action | Resin overcoat/barrier which yields a 20%-30% Peroxide releasing whitening effect (once Alcohol is evaporated) | Peroxide Gel which leaves a goo residue that is broken down once moisture comes in contact. DOES NOT ADHERE TO TEETH. |
| Time of Effectiveness Efficacy (Apply 2 times per day for 14 days) | 20 minute peroxide releasing compound - Sustained effervescence 4 shades (up to 8) of whitening using value oriented Vita shade guide | Breaks down after only a few minutes once moisture contacts solution. Only 3.2 shades of whitening |

Superior Whitening Results

Clinical study of inventive whitening agent obtained whitening results of up to 8 shades (average of 4 shades) in two weeks using a conservative protocol. Other brush-on whitening products do not adhere to the tooth for an extended period of time. These other conventional products typically wash off (wear off) the user's teeth within five minutes after application. Inventive whitening compound forms a precipitant on the tooth that releases peroxide for about 20 minutes. The conventional whitening product breaks down once moisture is in contact with the whitening compound.

The preferred composition is composed of about 9% (by weight) Carbamide Peroxide in an alcohol base. Once the whitening composition is applied to the tooth, the alcohol evaporates leaving a precipitant that yields approximately 20%-30% carbamide.

Easier to Use

As the inventive whitening compound utilizes a resin that forms a peroxide releasing precipitant which adheres to the tooth (even when moisture is present), there is no need to dry the teeth prior to use. In contrast, conventional agents use a gel-based compound that forms a "goo"-like layer on the teeth that is removed from the teeth when exposed to moisture. Thus, the user is required to carefully wipe the teeth dry prior to application.

Virtually No Tooth Sensitivity

Based on clinical study using the inventive whitening compound, participants experienced little, if any, tooth sensitivity. In traditional whitening gels and methods, glycerin and the use of a tray to cover the harsh compound dehydrates the tooth thus causing sensitivity. As inventive product does not use a tray or other typical chemicals found in gels, tooth sensitivity will not be present. In the clinical study of the conventional product compared above, tooth sensitivity is similar to other whitening products.

Better Chemical Composition

The inventive compound's coating, peroxide composition forms a film (resin) that adheres to the teeth. The film can easily be removed from the teeth by brushing or the film will wear off after about 3-4 hours. In contrast, the conventional product compared above uses a chemical composition similar to other gel-based whitening products.

Alternative Embodiment of Whitening Compound

A small heat-emitting hand-held "pen light" may be used to further activate the whitening compound. This light would be used by the user and need not be used by a dentist or other professional to perform this function. Such allows for the resin to be applied in a manner that will create a semi-solid and form a thicker film over the user's teeth. The user would apply this at night, for example, and brush the whitening compound off in the morning. The peroxide compound may be the heat-actuated whitening agent in this case.

The resin will create a thick film on the user's tooth allowing the whitening agent to be released for an extended period of time of about 40 minutes. That extended release period allows the user to apply the whitening compound once per day and achieve the same whitening results as the other formulation.

Yet Another Embodiment Application of Whitening Compound

As the inventive compound utilizes a resin to cause the whitening compound to adhere to the user's tooth, more resin can be used in the formulation, thus creating a thicker film on the user's tooth, which film will allow the whitening agent to be released on the tooth for approximately 20-40 minutes or more. This formulation could include: PEG 400, synthetic resin and urea hydrogen peroxide.

The inventive method also comprises a novel active ingredient imbedded in or carried by a novel carrier that permits sustainable release of the active ingredient and that would be painted on or brushed on the tooth surface and would remain active for a period of time.

The adhesive or resin may be synthetic or natural. The resin may be a rosin.

The rosin may be a refined hydrogenated rosin such as supplied by Hercules Chemical, Pinova Division, Brunswick, Ga., U.S.A., as described above.

The whitening agent may be any peroxide derivative or other chemical component that would whiten teeth. The whitening agent may be provided in varying concentrations depending on the carrier in which the agent is provided, as well as depending on the degree of whitening required, the physical properties of the teeth, and the like. For example, urea hydrogen peroxide, C.A.S. No. 124-43-6, supplied by Professional Compounding Centers of America of Houston, Tex. may be used as described above.

Other known peroxides may be substituted for the above-described peroxides.

Sodium bicarbonate may be substituted for peroxide(s) as the whitening agent.

It is contemplated that the whitening compound will be selected so that the whitening agent and the carrier will yield a release of the whitening agent to the tooth surface over time. This optional time-release mechanism may be for less than a few minutes to ten (10) hours or more.

The hydroxypropyl cellulose may be as supplied by Professional Compounding Centers of America, Houston, Tex.; e.g., hydroxypropyl cellulose 1500 cps, C.A.S. No. 9004-64-2, part no. 30-1996-100, Lot No. 26855, obtained in a 100 g lot, and used as described above.

The spearmint oil may be Spearmint Oil N.F (i.e., National Formulary), supplied by Professional Compounding Centers of America (P.C.C.A.), Houston, Tex., Part No. 30-1178-30 used as described above.

Embodiments of FIGS. 10-12

FIGS. 10 and 11 illustrate another embodiment of a tooth whitening delivery system 190 according to a first preferred embodiment of the invention.

Tooth whitening system 190 includes a container 200 for holding a whitening agent or whitening compound 260. Container 200 may be provided with a resealable opening 216 for repeated access to the inside and, hence, the contents of container 200.

An applicator body, such as the illustrated cylinder 226 may be provided for applying the whitening agent held in container 200.

Cylinder 226 may be configured for being held by a user when applying the whitening agent to the user's teeth.

Container 200 may be disposable, or may take another form, as described below.

When whitening agent 260 is in its semi-solid or solid state, such as at ambient temperature, a movable actuator 220 provided on body 200 my be actuated to dispense a desired quantity of whitening compound 260 from container 200. For example, actuator 220 may be in the form of a rotatable actuator which rotates relative to cylinder 260 and forces an amount of whitening compound 260 out of container 200 as a function of the amount of rotation of actuator 22. Body 200 and actuator 220 may be in the form of conventional lip balm dispenser or the type which dispenses solid lip balm at ambient temperatures. As shown, a quantity 228 of whitening compound 220 has been dispensed thanks to use of actuator 220, and whitening compound 260 is being applied to a user's tooth (or teeth) in use. The embodiment of FIGS. 10 and 11 may be used for dispensing viscous, solid or semi-solid tooth-whitening compound 260 according to the invention. The size and configuration of opening 216 may be varied depending on the intended use and the viscosity of the solid or semi-solid whitening compound to be dispensed, as will be readily appreciated.

A cap 230 may be provided to cover opening 216 of container 200 when not in use.

FIG. 11 illustrates the user's or user's jaw 40 including an upper jaw 44 and a lower jaw 48.

Teeth 50 include an outer surface 52.

Outer surface 52 is shown being whitened by use of the whitening agent 260, as it is outer surface 52 which is typically visible when the user's lips are drawn back exposing teeth 50.

FIG. 11 illustrates how container 200 is used when applying the whitening agent on outer surface 52 of teeth 50. It should be noted that exposed, dispensed quantity 228 of whitening compound 260 may be configured and sized so as to reach all exposed surfaces of teeth 50. Preferably, the viscosity of compound 260 is selected so that the whitening agent 260 may be applied directly to all the exposed tooth surfaces which the user desires to whiten. In use, the user may dispense a desired quantity 228 of whitening compound 260, hold container 200 as shown in FIG. 11, and apply sufficient pressure to force whitening compound 260 into crevices 262, for example, as desired, in a manner analogous to that described above in connection with the other embodiments. One or more teeth 50 may have whitening compound 60 applied to them.

A single coat or multiple coats or layers of whitening agent 260 may be applied.

Whitening agent 260 is formulated so that it need not be covered, in use, by a device, such as a tray or tape, as the formulation is selected so that contact of whitening agent 260 with the mouth tissue causes little or no discomfort nor harm to the mouth tissue.

Whitening agent 260 of FIGS. 10-11 has been successfully used with only one layer of compound 260 as the whitening agent, as in the embodiments above.

FIG. 12 illustrates another preferred embodiment of a whitening system 300 according to the invention. Whitening system 300 includes a container 304 having an opening 306 for providing access to the contents of container 304. Additional openings 306 may be provided, depending on the intended use.

Container 304 may be provided with a semi-solid viscous whitening material 308 which may differ in viscosity from the first material or whitening agent 260. The second whitening material or compound 308 may be dispensed in the illustrated flexible container 304, or may be dispensed in the typically relatively rigid container 200 of FIGS. 10 and 11. Threads 312 may be provided to detachably secure a cover for covering hole 306.

The second whitening material 308 may be applied to teeth 50 as follows. The user squeezes container 304 sufficiently so as to cause a desired quantity of semi-solid whitening agent 308 to exit opening 306.

Typically, a user will find it unnecessary to whiten the inner surfaces 54 of his or her incisors 124, as the inner surfaces of the user's incisors 124 are rarely visible to others, for example.

The embodiments of FIGS. 7-9 may be used with any of the dispensers of FIGS. 1-6 or 10-12. In such a case, the user may dispense a desired quantity of the respective solid whitening agent or semi-solid whitening agent (or agents) onto applicator 150 or 170, respectively, for example.

As will be appreciated, the viscosity of the whitening agent may be selected so that not only is the whitening agent semi-solid or solid at ambient temperatures, but the whitening agent is also at least semi-solid when applied to the users' teeth in the mouth environment. The temperature of the mouth will typically be 37° C. (98.6° F.).

In use, it is contemplated that the whitening compounds described herein may be applied by hand, such as by applying the whitener to a fingertip then daubing on the whitening compound with the user's fingertip(s).

It is contemplated that in any of the above-described embodiments, any suitable viscous, solid or semi-solid whitening agent may be used that can whiten without irritating the mouth tissues.

The solid or semi-solid whitening compound can be made in several ways.

Whitening Agent Composition D2

In one inventive embodiment the whitening compound may comprise in weight percent:

Urea Peroxide 15%
Rosin 5%
Wax 79.8%
Stevia Powder 0.15%
Peppermint Oil 0.05%

The urea peroxide and resin can be incorporated in a wax resin formulation and then pressed or extruded into the desirable shape and manufactured in the dispenser.

The dispensing device would cause the whitening compound to protrude as a solid or semi-solid and the consumer would directly apply the solid or semi-solid compound onto the tooth surface in a manner similar to lip-stick. It may be desirable to provide several shapes and sizes of dispensers or applicators to apply whitening compound to the entire facial surface of the tooth and interproximal areas. If saliva on the tooth hinders the resin-wax whitening compound from sticking to the tooth surface a hydrophilic substance can be incorporated in the compound to absorb the moisture as the whitening compound is being applied.

With this invention it will be unnecessary to dry the tooth prior to application and will be unnecessary to keep the lips and cheek away from the tooth surface immediately after application, unlike in prior art whitening compounds.

Whitening Agent Composition D3

Another whitening agent composition may comprise:
Carbamide Peroxide AIC product code: RPLGC30025KBXH
AIC U.S.A.
RANGE: 0.01-30 gm
Foral NC—Hydrogenated Rosin
Hercules Chemical, U.S.A.
RANGE: 0.01-30 gm
Stevia 90% powder (sweetener)
JAJA—Allen Weber, U.S.A.

RANGE: 0.001-2.0 gm
Peppermint Oil
Rainbow Gardens, U.S.A.
RANGE: 0.001-2.0 gm
KLUCEL HF Pharma hydroxypropylcellulose
Hercules—Aqualon Division Wilmington, Del., U.S.A.
RANGE: 0.001-25 gm
Ethyl Alcohol 95% 190 proof
RANGE: 10-50 ml.

As an example of viscosity ranges contemplated for the inventive compounds, depending on the intended use, such viscosities being determined in a 25° C. environment as follows.

Viscosity: Brookfield Viscometer DV1+(RVT)
Spindle 5 @12 RPM (25° C.)
Preferred Product Range: 400-800 cps (preferably about 600 cps).
Upper Range: 3000-5000 cps (semi-solid-gel) to a solid unflowable formulation, i.e., a solid which retains its solid form, such as a stick-like, cylindrical form similar to a conventional cylindrical colored lipstick or a conventional cylindrical lip balm protector, e.g., Chapstick® brand lip balm, A. H. Robbins Co., Richmond, Va., USA).

Features of Semi-Solid and Solid Whitening Compounds According to the Invention

With the present invention the consumer would simply remove the top of the applicator and then twist the lower part of the applicator and the semi-solid or solid whitening compound would protrude. The consumer would then apply the whitening compound directly onto the surface of the tooth.

The tooth would not need to be dried prior to application.

The whitening action would take place in a manner somewhat similar to that of previous brush-on whitening compounds. For example, the peroxide would be released from the solid by the moisture in the saliva along with the salivary proteins. As the compound is a solid rather than a liquid or gel the concentration of peroxide can be substantially increased, increasing the concentration beyond 30% is contemplated.

Having the whitening agent in a solid/semi-solid state offers several advantages over current whitening systems to date:
  Ease of consumer application: no mouth trays, adhesive strips, bottles or brushes.
  Can be applied anytime, anywhere.
  Will not cause any soft tissue irritation; the solid can only be applied to the tooth and will not run onto the soft tissues.
  Easy transported; the applicator and semi-solid or solid whitening compound can be carried in a purse or pocket.
  Affordable.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

The invention claimed is:

1. A method of whitening teeth, comprising:
a) providing a viscous whitening compound;
b) the viscous whitening compound being a viscous, solid whitening compound;
c) the viscous solid whitening compound including a whitening agent, and the whitening agent including by weight percent about 45% urea hydrogen peroxide;
d) the viscous solid whitening compound having a viscosity in a solid, unflowable formulation of about 5000 cps as measured by a Brookfield viscometer (spindle 5 @ 12 rpm at 25° Celsius);
e) providing a container for containing the viscous whitening compound, the container configured for being held by a user and including an actuator configured for forcing a dispensed quantity of the viscous whitening compound out of the container;
f) applying the dispensed quantity of the viscous solid whitening compound on a user's teeth;
g) the step of applying the dispensed quantity of the viscous solid whitening compound being performed by applying sufficient pressure on the dispensed quantity of the viscous solid whitening compound directly on a surface of the user's tooth with the container held by the user;
h) the container being a lipstick-type cylindrical dispenser; and
i) the step of applying the dispensed quantity of the viscous solid whitening compound on the user's teeth being performed by contacting the user's teeth only with the dispensed quantity of the viscous solid whitening compound.

2. A method as in claim 1, wherein:
a) said step of applying the viscous solid whitening compound is performed by applying the viscous solid whitening compound on a surface of a single one of the user's teeth.

3. A method as in claim 1, wherein:
a) a carrier is provided; and
b) the carrier includes a resin.

4. A method as in claim 3, wherein:
a) the resin is a non-toxic resin.

5. A method as in claim 3, wherein:
a) the resin is a synthetic resin.

6. A method as in claim 3, wherein:
a) the resin is a natural resin.

7. A method as in claim 1, wherein:
a) the viscous solid whitening compound includes an active whitening agent which is activatable by water from a tooth to which the viscous solid whitening compound is to be applied.

8. A method as in claim 1, wherein:
a) the viscous solid whitening compound includes a synthetic adhesive.

9. A method as in claim 1, wherein:
a) the viscous solid whitening compound adheres sufficiently long without the aid of a tape that the whitening agent can whiten a human tooth.

10. A method as in claim 1, wherein:
a) the viscous solid whitening compound comprising, by weight percent:

| | | |
|---|---|---|
| i) | Undenatured Ethanol | 15-85%; |
| ii) | Resin | 0.001-65%; and |
| iii) | Hydroxypropylcellulose | 0.001-20%. |

* * * * *